United States Patent [19]

Peyman

[11] Patent Number: 4,840,175
[45] Date of Patent: Jun. 20, 1989

[54] METHOD FOR MODIFYING CORNEAL CURVATURE

[76] Inventor: Gholam A. Peyman, 535 N. Michigan Ave., Chicago, Ill. 60611

[21] Appl. No.: 148,170

[22] Filed: Jan. 22, 1988

Related U.S. Application Data

[63] Continuation of Ser. No. 946,633, Dec. 24, 1986, abandoned, which is a continuation of Ser. No. 760,080, Jul. 29, 1985, abandoned.

[51] Int. Cl.$^4$ ............................................. A61N 5/06
[52] U.S. Cl. .................................................. 128/303.1
[58] Field of Search ..................... 128/303.1, 395–398, 128/362

[56] References Cited

U.S. PATENT DOCUMENTS

| | | |
|---|---|---|
| 4,445,892 | 5/1984 | Hussein et al. ............. 128/303.1 |
| 4,461,294 | 7/1984 | Baron ........................ 128/303.1 |
| 4,469,098 | 9/1984 | Davi .......................... 128/303.1 |
| 4,648,400 | 3/1987 | Schneider et al. .......... 128/303.1 |
| 4,665,913 | 5/1987 | L'Esperance, Jr. ......... 128/303.1 |
| 4,669,466 | 6/1987 | L'Esperance ............... 128/303.1 |
| 4,718,418 | 1/1988 | L'Esperance, Jr. ......... 128/303.1 |
| 4,729,372 | 3/1988 | L'Esperance, Jr. ......... 128/303.1 |
| 4,732,148 | 3/1988 | L'Esperance, Jr. ......... 128/303.1 |

OTHER PUBLICATIONS

"Excimer Laser Ablator of the Cornea & Lens", by C. Puliafito et al; Opthalmology, 6/85, vol. 92, #6, pp. 741-748.

"Excimer Laser Surgery of the Cornea", by S. Trokel et al.; Am. J. Opthal., vol. 96, pp. 710-715, 1983.

"Corneal Surgery", by L. Girard; The C. V. Mosby Publishing Company, London, 1981; pp. 84, 107-110, 114, 116, 123, 125-133, 143-171.

"Response of the Corneal Epithelium to KrF Excimer Laser Pulses", J. Taboda et al., Health Physics, vol. 40, pp. 677-683, (1981).

"IBM's Heatless Laser Etching: A Hot IC & Medical Prospect", News Spectra, 6/83.

"Heatless Laser Etching", by J. Free: Popular Science, 12/83, p. 124.

Primary Examiner—Lee S. Cohen
Assistant Examiner—David Shay
Attorney, Agent, or Firm—Roylance, Abrams, Berdo & Goodman

[57] ABSTRACT

A method and apparatus for modifying the curvature of a live cornea via use of an excimer laser. The live cornea has a thin layer removed therefrom leaving an exposed internal surface thereon. Then, either the surface or thin layer is exposed to the laser beam along a predetermined pattern to ablate desired portions. The thin layer is then replaced onto the surface. Ablating a central area of the surface or thin layer makes the cornea less curved, while ablating an annular area spaced from the center of the surface or layer makes the cornea more curved. The desired predetermined pattern is formed by use of a variable diaphragm, a rotating orifice of variable size, a movable mirror or a movable fiber optic cable through which the laser beam is directed towards the exposed internal surface or removed thin layer.

5 Claims, 3 Drawing Sheets

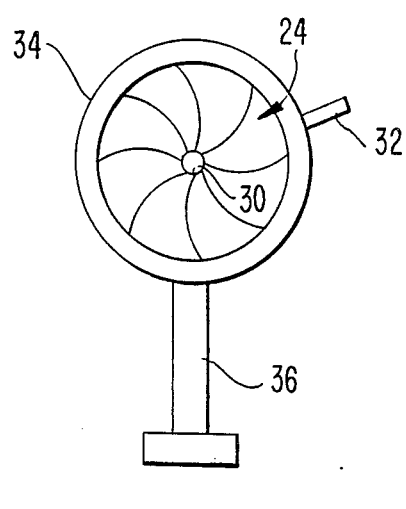
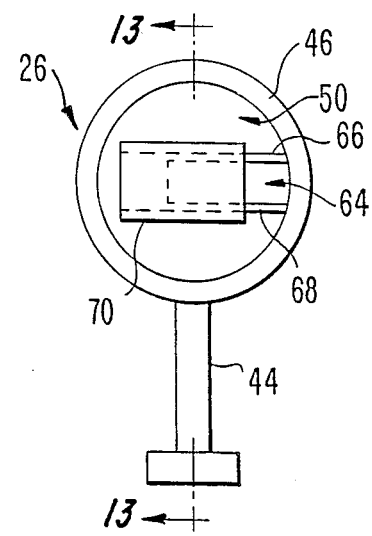
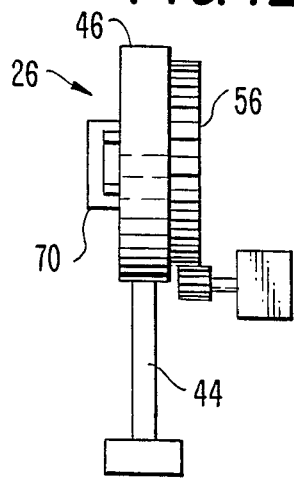
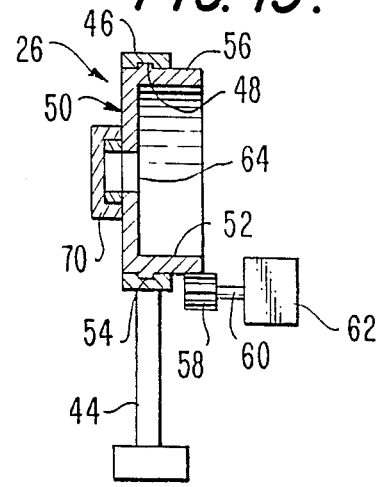
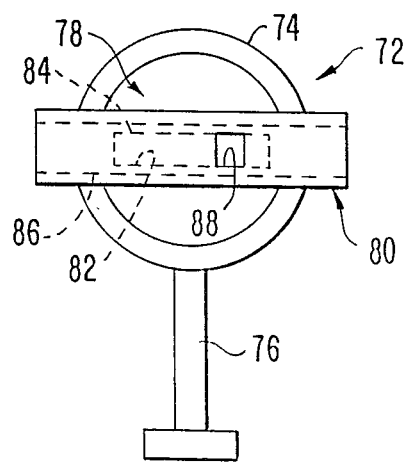

METHOD FOR MODIFYING CORNEAL CURVATURE

This is a continuation of application Ser. No. 946,633 filed Dec. 24, 1986, now abandoned, which is a continuation of application Ser. No. 760,080 filed July 29, 1985, now abandoned.

FIELD OF THE INVENTION

The invention relates to a method and apparatus for modifying the curvature of a live cornea via a laser beam.

BACKGROUND OF THE INVENTION

In an emetropic human eye, the far point, i.e., infinity, is focused on the retina. Ametropia results when the far point is projected either in front of the retina, i.e., myopia, or in the back of this structure, i.e., hypermetropic or hyperopic state.

In a myopic eye, either the axial length of the eye is longer than in a normal eye, or the refractive power of the cornea and the lens is stronger than in emetropic eyes. In contrast, in hypermetropic eyes the axial length may be shorter than normal or the refractive power of the cornea and lens is less than in a normal eye. Myopia begins generally at the age of 5-10 and progresses up to the age of 20-25. High myopia greater than 6 diopter is seen in 1-2% of the general population. The incidence of low myopia of 1-3 diopter can be up to 10% of the population.

The incidence of hypermetropic eye is not known. Generally, all eyes are hypermetropic at birth and then gradually the refractive power of the eye increases to normal levels by the age of 15. However, a hypermetropic condition is produced when the crystalline natural lens is removed because of a cataract.

Correction of myopia is achieved by placing a minus or concave lens in front of the eye, in the form of glasses or contact lenses to decrease the refractive power of the eye. The hypermetropic eye can be corrected with a plus or convex set of glasses or contact lenses. When hypermetropia is produced because of cataract extraction, i.e., removal of the natural crystalline lens, one can place a plastic lens implant in the eye, known as an intraocular lens implantation, to replace the removed natural crystalline lens.

Surgical attempts to correct myopic ametropia dates back to 1953 when Sato tried to flatten the corneal curvature by performing radial cuts in the periphery of a corneal stroma (Sato, Am. J. Ophthalmol. 36:823, 1953). Later, Fyoderov (Ann. Ophthalmol. 11:1185, 1979) modified the procedure to prevent postoperative complications due to such radial keratotomy. This procedure is now accepted for correction of low myopia for up to 4 diopter (See Schachar [eds] Radial Keratotomy LAL, Pub. Denison, Texas, 1980 and Sanders D [ed] Radial Keratotomy, Thorofare, NJ, Slack publication, 1984).

Another method of correcting myopic ametropia is by lathe cutting of a frozen lamellar corneal graft, known as myopic keratomileusis. This technique may be employed when myopia is greater than 6 diopter and not greater than 18 diopter. The technique involves cutting a partial thickness of the cornea, about 0.26-0.32 mm, with a microkeratome (Barraquer, Ophthalmology Rochester 88:701, 1981). This cut portion of the cornea is then placed in a cryolathe and its surface modified. This is achieved by cutting into the corneal parenchyma using a computerized system. Prior to the cutting, the corneal specimen is frozen to −18° F. The difficulty in this procedure exists in regard to the exact centering of the head and tool bit to accomplish the lathing cut. It must be repeatedly checked and the temperature of the head and tool bit must be exactly the same during lathing. For this purpose, carbon dioxide gas plus fluid is used. However, the adiabatic release of gas over the carbon dioxide liquid may liberate solid carbon dioxide particles, causing blockage of the nozzle and inadequate cooling.

The curvature of the corneal lamella and its increment due to freezing must also be calculated using a computer and a calculator. If the corneal lamella is too thin, this results in a small optical zone and a subsequent dissatisfactory correction. If the tissue is thicker than the tool bit, it will not meet at the calculated surface resulting in an overcorrection.

In addition, a meticulous thawing technique has to be adhered to. The complications of thawing will influence postoperative corneal lenses. These include dense or opaque interfaces between the corneal lamella and the host. The stroma of the resected cornea may also become opaque (Binder Arch Ophthalmol 100:101, 1982 and Jacobiec, Ophthalmology [Rochester] 88:1251, 1981; and Krumeich JH, Arch, AOO, 1981). There are also wide variations in postoperative uncorrected visual acuity. Because of these difficulties, not may cases of myopic keratomileusis are performed in the United States.

Surgical correction of hypermetropic keratomyclosis involves the lamellar cornea as described for myopic keratomyelosis. The surface of the cornea is lathe cut after freezing to achieve higher refractive power. This procedure is also infrequently performed in the United States because of the technical difficulties and has the greatest potential for lathing errors. Many ophthalmologists prefer instead an alternative technique to this procedure, that is keratophakia, i.e., implantation of a lens inside the cornea, if an intraocular lens cannot be implanted in these eyes.

Keratophakia requires implantation of an artificial lens, either organic or synthetic, inside the cornea. The synthetic lenses are not tolerated well in this position because they interfere with the nutrition of the overlying cornea. The organic lenticules, though better tolerated, require frozen lathe cutting of the corneal lenticule.

Problems with microkeratomies used for cutting lamellar cornea are irregular keritectomy or perforation of the eye. The recovery of vision is also rather prolonged. Thus, significant time is needed for the implanted corneal lenticule to clear up and the best corrective visions are thereby decreased because of the presence of two interfaces.

Application of ultraviolet and shorter wavelength lasers also have been used to modify the cornea. These lasers are commonly known as excimer lasers which are powerful sources of pulsed ultraviolet radiation. The active medium of these lasers are composed of the rare gases such as argon, krypton and xenon, as well as the halogen gases such as fluorine and chlorine. Under electrical discharge, these gases react to build excimer. The stimulated emission of the excimer produces photons in the ultraviolet region.

Previous work with this type of laser has demonstrated that far ultraviolet light of argon-fluoride laser light with the wavelength of 193 nm. can decompose organic molecules by breaking up their boundings. Because of this photoablative effect, the tissue and organic and plastic material can be cut without production of heat, which would coagulate the tissue. The early work in ophthalmology with the use of this type of laser is reported for performing radial cuts in the cornea in vitro (Trokel, Am. J. Ophthalmol 1983 and Cotliar, Ophthalmology 1985). Presently, all attempts to correct corneal curvature via lasers are being made to create radial cuts in the cornea for performance of radial keratotomy and correction of low myopia.

Because of the problems related to the prior art methods, there is a continuing need for improved methods to correct eyesight.

SUMMARY OF THE INVENTION

Accordingly, it is a primary object of the present invention to provide a method and apparatus for modifying corneal curvature without coagulating the corneal structure.

Another object of the invention is to provide such a method and apparatus that can modify the curvature of a live cornea, thereby eliminating the need and complications of working on a frozen cornea.

Another object of the invention is to provide a method and apparatus for improving eyesight without the use of glasses or contact lenses, but rather by merely modifying the corneal curvature.

Another object of the invention is to provide a method and apparatus for modifying corneal curvature by using a source of laser light in a precise manner.

The foregoing objects are basically attained by providing a method of modifying the curvature of a live cornea comprising the steps of removing a thin layer from the front of the cornea and thereby exposing an internal surface thereof, directing a laser beam onto the surface or the thin layer in a predetermined pattern to ablate a portion thereof, and replacing the originally removed thin corneal layer back onto the surface.

Ablating a central area of the surface or thin layer makes the cornea less curved, while ablating an annular area spaced from the center of the surface or layer makes the cornea more curved.

The foregoing objects are also basically attained by providing an apparatus for modifying the curvature of a live cornea having a thin corneal layer separated therefrom and leaving an exposed internal surface thereon, the combination comprising: a laser beam source; and means, interposed between the surface or the thin corneal layer, for directing the laser beam onto the surface or the thin corneal layer in a predetermined pattern to ablate a portion thereof, the thin corneal layer being replaced onto the surface after ablation, thereby modifying the curvature of the overall cornea.

The desired predetermined pattern is formed by use of a variable diaphragm, a rotating orifice of variable size, a movable mirror or a movable fiber optic cable through which the laser beam is directed towards the exposed internal surface or removed thin layer.

Other objects, advantages, and salient features of the present invention will become apparent from the following detailed description, which, taken in conjunction with the annexed drawings, discloses preferred embodiments of the invention.

DRAWINGS

Referring now to the drawings which form a part of this original disclosure:

FIG. 10 is a front elevational view of the adjustable diaphragm shown in FIG. 3 used for directing the laser beam towards the eye;

FIG. 11 is a front elevational view of the guiding mechanism shown in FIG. 3 having a rotatable orifice of variable size formed therein, for directing the laser beam towards the eye in a predetermined pattern;

FIG. 12 is a right side elevational view of the guiding mechanism shown in FIG. 11;

FIG. 13 is a right side elevational view in section taken along line 13—13 in FIG. 11 showing the internal parts of the guiding mechanism;

FIG. 14 is a front elevational view of a modified guiding mechanism including a movable orifice;

DETAILED DESCRIPTION OF THE INVENTION

Figure 1:
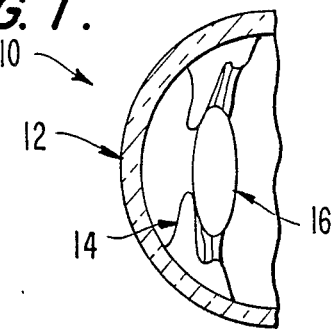
FIG. 1 is a side elevational view in section taken through the center of an eye showing the cornea, pupil and lens.
Figure 2:
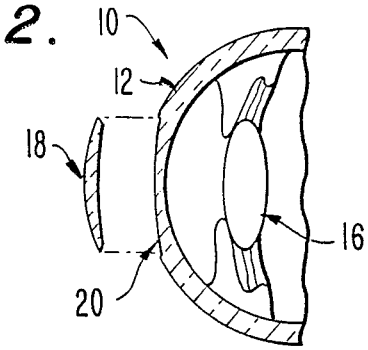
FIG. 2 is a side elevational view in section similar to that shown in FIG. 1 except that a thin layer has been removed from the front of the cornea, thereby exposing an internal surface thereof.
Figure 18:
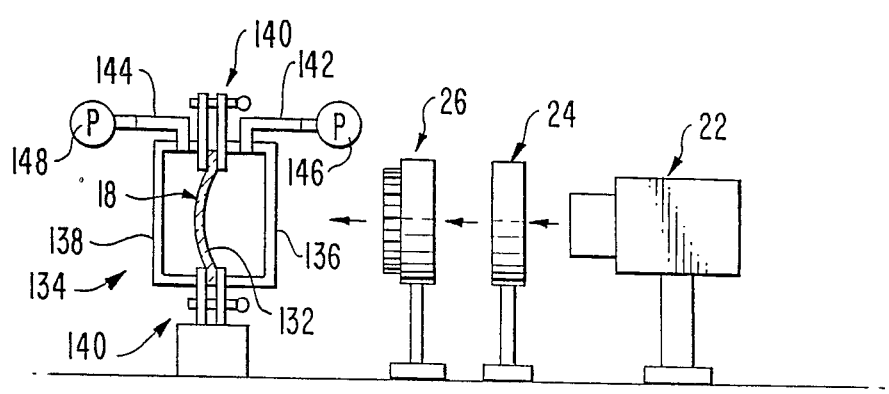
FIG. 18 is a diagrammatic side elevational view of a laser source, diaphragm and guiding mechanism for use in ablating the thin layer removed from the cornea, which is shown supported by a pair of cups.

As seen in FIG. 1, an eye 10 is shown comprising a cornea 12, a pupil 14, and a lens 16. If the combination of the cornea and lens does not provide adequate vision, the cornea can be modified in accordance with the invention to modify the refractive power of the combined corneal and lens system, to thereby correct vision. This is accomplished first by removing a thin layer 18 from the center part of the cornea 12 by cutting, this thin layer being on the order of about 0.2 mm in thickness with the overall cornea being about 0.5 mm in thickness. Once the thin layer 18 is cut and removed from the cornea, it exposes an internal surface 20 on the remaining part of the cornea resulting from the surgical procedure. Advantageously, it is this exposed internal surface 20 that is the target of the ablation via the excimer laser. On the other hand, the cut surface on the removed thin layer of the cornea can also be the target of the laser, as illustrated in FIG. 18 and discussed in further detail hereinafter.

Figure 3:
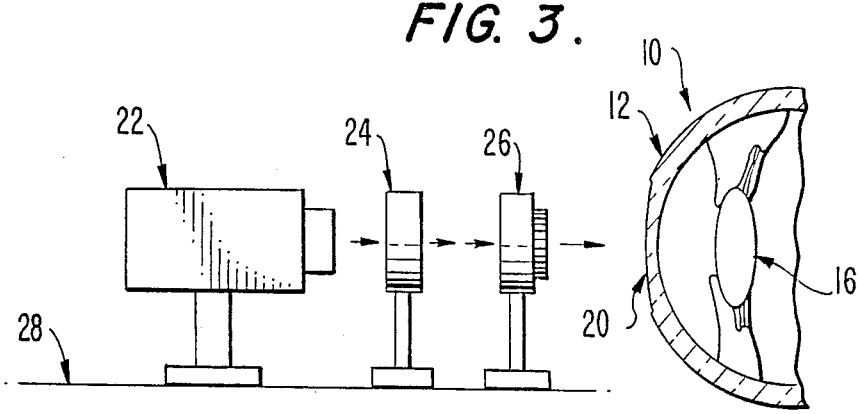
FIG. 3 is a diagrammatic side elevational view of the eye shown in FIG. 2 with a laser beam source, diaphragm and guiding mechanism being located adjacent thereto.

As seen in FIG. 3, the apparatus used in accordance with the invention comprises a laser beam 22, an adjustable diaphragm 24, and a guiding mechanism 26, all aligned adjacent the eye 10 and supported on a suitable base 28.

The laser beam 22 is advantageously an excimer laser of the argon-fluoride or krypton-fluoride type. This type of laser will photoablate the tissue of the cornea, i.e., decompose it without burning or coagulating which would unduly damage the live tissue. This ablation removes desired portions of the cornea and thereby allows for modification of the curvature thereof.

The adjustable diaphragm 24 seen in FIGS. 3 and 10 is essentially a conventional optical diaphragm with an adjustable central orifice 30 that can be increased or decreased in radial size by a manipulation of a lever 32 coupled to the diaphragm. The diaphragm is advantageously supported in a ring 34 that is in turn supported on a stand 36 on base 28. The material forming the diaphragm is opaque to laser light and thus when the laser is directed towards the diaphragm, it will pass therethrough only via the orifice 30. The diaphragm 24 can be used in conjunction with the guiding mechanism 26, to be described in more detail hereinafter, to restrict the size of the laser beam passing to the guiding mechanism 26, or it can be used by itself to provide ablation of the exposed internal surface 20 of a cornea at its center.

Figure 7:
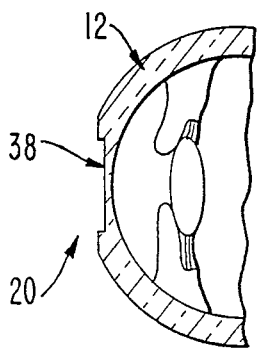
FIG. 7 is a side elevational view in section of an eye which has been ablated in the central area of the exposed internal surface on the cornea.
Figure 8:
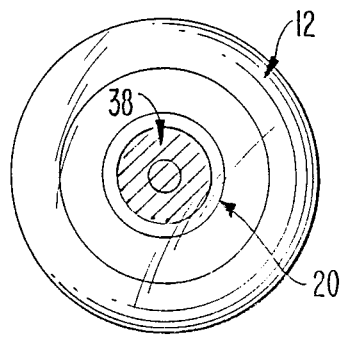
FIG. 8 is a front elevational view of the cornea having the central ablated portion shown in FIG. 7.
Figure 9:
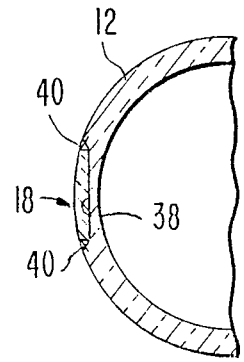
FIG. 9 is a side elevational view in section of the ablated cornea of FIGS. 7 and 8 in which the thin layer previously removed from the cornea is replaced over the ablated area, thereby reducing the curvature of the overall cornea.

This is illustrated in FIGS. 7-9 where a substantially disc-shaped ablated portion 38 is formed in the central exposed internal surface 20 by directing the laser beam 22 through orifice 30 of the diaphragm 24. By modifying the size of the orifice, the disc-shaped ablated portion 38 can be varied in size. Also, by varying the size of the orifice over time, either a concave or convex ablated portion can be formed, as desired. As shown in FIG. 9, once the ablated portion 38 is as desired, the previously removed thin layer 18 is replaced onto the cornea in the ablated portion 38 and can be connected thereto via sutures 40.

Because the ablated portion 38 as seen in FIG. 7 is essentially a uniform cylindrical depression in the exposed internal surface 20, when the thin corneal layer 18 is replaced, the curvature of the cornea is decreased, thereby modifying the refractive power of the cornea and lens system.

As seen in FIG. 10, lever 32 is used to vary the size of orifice 30, and is capable of being manipulated by hand or by a suitable conventional motor, which can be coordinated to provide an expansion or contraction of the orifice as necessary over time.

As seen in FIGS. 3, 11, 12 and 13, the guiding mechanism 26 can be utilized in addition to or in place of the diaphragm 24 to guide the laser light onto the cornea. This guiding mechanism 26 is especially advantageous for forming an annular ablated portion 42 in surface 20 as seen in FIGS. 4-6 for increasing the overall curvature of the cornea.

Figure 4:
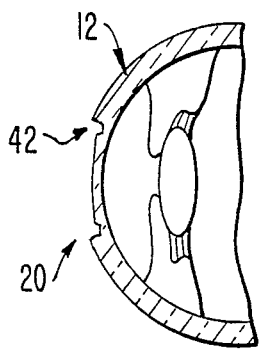
FIG. 4 is a side elevational view in section of an eye that has been treated by the apparatus shown in FIG. 3 with ablation conducted in an annular area spaced from the center of the exposed internal surface on the cornea.
Figure 5:
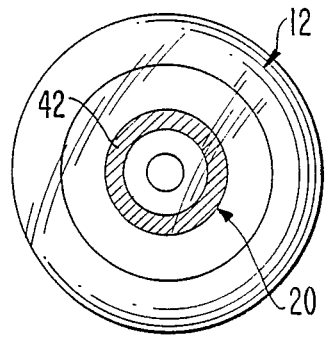
FIG. 5 is a front elevational view of the ablated cornea shown in FIG. 4.
Figure 6:
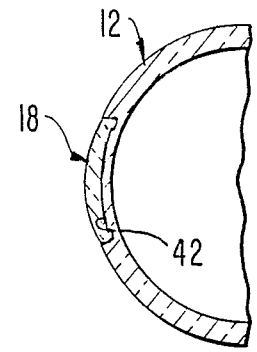
FIG. 6 is a side elevational view in section showing the ablated cornea of FIGS. 4 and 5 with the thin layer previously removed from the cornea replaced onto the ablated area in the cornea, thereby increasing the curvature of the overall cornea.

As seen in FIGS. 4 and 5, this annular ablated portion 42 is spaced from the center of the exposed internal surface 20 and when the previously removed thin corneal layer 18 is replaced and sutured, the thin layer tends to be more convex, thereby modifying the overall curvature of the cornea.

As seen in FIGS. 11-13, the guiding mechanism 26 comprises a stand 44 supporting a ring 46, this ring having a radially inwardly facing recess 48 therein. A disc 50, which is opaque to laser light, is located inside the ring and has a cylindrical extension 52 with an outwardly facing flange 54 rotatably and slidably received in the recess. On the cylindrical extension 52 which extends past ring 46 is an exterior toothed gear 56 that is in engagement with a pinion 58 supported on a shaft 60 of a motor 62. Rotation of pinion 58 in turn rotates gear 56 and disc 50.

The disc 50 itself has an elongated rectangular orifice 64 formed therein essentially from one radial edge and extending radially inwardly past the center point of the disc. Adjacent the top and bottom of the orifice 64 are a pair of parallel rails 66 and 68 on which a masking cover 70, which is U-shaped in cross section, is slidably positioned. Thus, by moving the masking cover 70 along the rails, more or less of the orifice 64 is exposed to thereby allow more or less laser light to pass therethrough and onto the cornea. Clearly, the larger the orifice, the larger the width of the annular ablated portion 42 will be. By rotating the disc, the orifice 64 also rotates and thus the annular ablated portion 42 is formed.

Referring now to FIG. 14, a modified guiding mechanism 72 is shown which is similar to guiding mechanism 26 shown in FIGS. 11-13 except that the size of the orifice is not variable. Thus, the modified guiding mechanism 72 is comprised of a ring 74 on a stand 76, an opaque disc 78 which is rotatable in the ring via a suitable motor, not shown, and a slidable masking cover 80. Disc 78 has a rectangular orifice 82 extending diametrically thereacross with parallel rails 84 and 86 on top and bottom for slidably receiving the masking cover 80 thereon, this cover being U-shaped for engagement with the rails. The masking cover 80 has its own orifice 88 therein which aligns with orifice 82 on the disc. Thus, by sliding the masking cover 80 along the rails of the disc, the location of the intersection of orifice 88 and orifice 82 can be varied to vary the radial position of the overall through orifice formed by the combination of these two orifices. As in guiding mechanism 26, the masking cover 80 and disc 78 are otherwise opaque to laser light except for the orifices.

Figure 15:
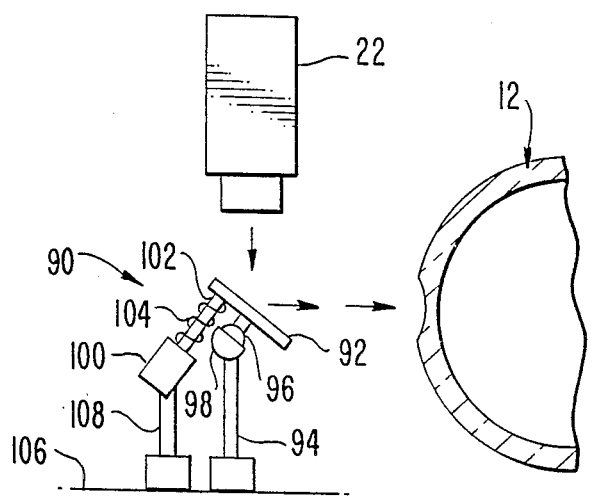
FIG. 15 is a diagrammatic side elevational view of a second modified guiding mechanism for a laser beam including a universally supported mirror and actuating motors used for moving the mirror and thereby guiding the laser beam in the predetermined pattern.

Referring now to FIG. 15, a second modified guiding mechanism 90 is shown for directing laser light from laser beam source 22 to the cornea 12 along the desired predetermined pattern. This guiding mechanism 90 comprises a mirror 92 universally supported on a stand 94 via, for example, a ball 96 and socket 98 joint. This mirror 92 can be pivoted relative to the stand through the universal joint by means of any suitable devices, such as two small piezo-electric motors which engage the mirror at 90° intervals. For example, such a piezo-electric motor 100 having a plunger 102 coupled thereto and engaging the rear of the mirror can be utilized with a spring 104 surrounding the plunger and maintaining the mirror in a null position. The motor 100 is rigidly coupled to a base 106 via a stand 108. The second piezo-electric motor, not shown, can be located so that its plunger engages the rear of the mirror 90° from the location of motor 100. By using these two motors, springs and plungers, the mirror 92 can be fully rotated in its universal joint to direct the laser beam from source 22 onto the cornea 12 to ablate the cornea in a predetermined pattern.

Figure 16:
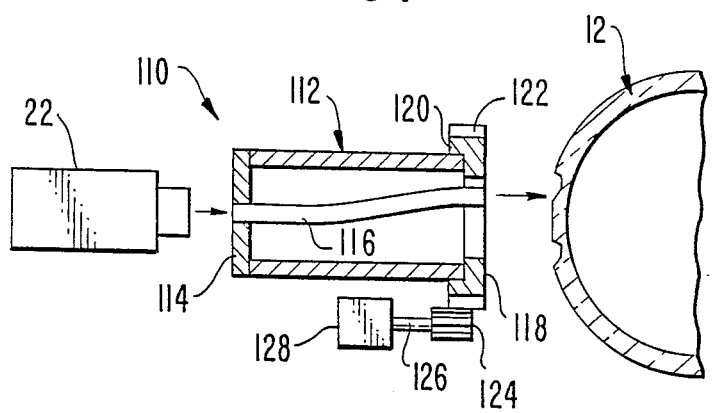
FIG. 16 is a diagrammatic side elevational view of a third modified guiding mechanism comprising a housing and a rotatable fiber optic cable.
Figure 17:
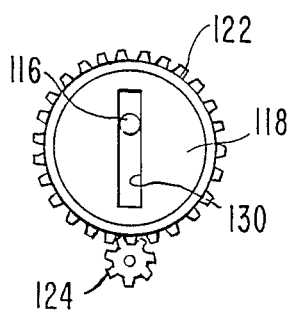
FIG. 17 is an end elevational view of the housing and fiber optic cable shown in FIG. 16.

Referring now to FIGS. 16 and 17, a third modified guiding mechanism 110 is shown for ablating a cornea 12 via directing laser light from laser source 22. This modified guiding mechanism 110 basically comprises a cylindrical housing 112 having an opaque first end 114 rotatably receiving the end of a fiber optic cable 116 therein. The second end 118 of the housing comprises a rotatable opaque disc having a flange 120 engaging the housing and an external gear 122 which in turn engages pinion 124, which is driven via shaft 126 and motor 128. Thus, rotation of the pinion results in rotation of gear 122 and thus the opaque second end 118 of the housing. This second end 118 has a diametrically oriented rectangular orifice 130 therein which receives the other end of the fiber optic cable 116 therein. That end of the fiber optic cable is either dimensioned so that it fits fairly tightly into the orifice or there is an additional suitable assembly utilized for maintaining the fiber optic cable end in a predetermined position in the orifice during rotation of the second end. However, this end would be movable radially of the orifice to change the position of the annular ablated portion formed by utilizing this guiding mechanism.

Referring now to FIG. 18, rather than ablating the exposed internal surface 20 on the cornea 12, the inner surface 132 of the removed thin corneal layer 18 can be ablated utilizing the apparatus shown in FIG. 18. Likewise, the apparatus of FIG. 18 can be used on an eye bank cornea removed from the eye and then positioned in the patient's eye to modify the curvature of the patient's combined corneal structure. This apparatus as before includes the source of the laser light 22, an adjustable diaphragm 24, and a guiding mechanism 26. In addition, an assembly 134 is utilized to support the rather flimsy removed thin corneal layer. This assembly 134 comprises a pair of laser light transparent cups 136 and 138 that are joined together in a sealing relationship via clamps 140 and engage therebetween the outer periphery of the thin corneal layer 18. Each of the cups has an inlet pipe 142, 144 for injecting pressurized air or suitable fluid into each via pumps 146 and 148. By using this pressurized container, the thin corneal layer 18 is maintained in the desired curvature so that the laser beam can provide a precise ablated predetermined pattern therein. In order to maintain the curvature shown in FIG. 8, the pressure on the right hand side of the thin layer is slightly greater than that on the left hand side.

Once the thin corneal layer 18 is suitably ablated as desired, it is replaced on the exposed internal surface 20 of the cornea and varies the curvature of the overall cornea as described above and illustrated in FIGS. 4–9.

While various advantageous embodiments have been chosen to illustrate the invention, it will be understood by those skilled in the art that various changes and modifications can be made therein without departing from the scope of the invention as defined in the appended claims.

What is claimed is:

1. A method of modifying the curvature of a patient's live cornea comprising the steps of
    removing a thin layer from the front of the live cornea and thereby exposing an internal surface thereof,
    directing a laser beam onto the exposed internal surface in a predetermined pattern to ablate, and therefrom remove, a three-dimensional portion thereof, and
    replacing the originally removed thin corneal layer back onto the ablated internal surface of the live cornea from which the thin corneal layer was removed,
    the removing, directing and replacing steps taking place without freezing the internal surface or the thin layer.

2. A method according to claim 1, wherein the replacing step includes the step of
    suturing the thin corneal layer to the cornea.

3. A method according to claim 1, wherein the directing step comprises the step of
    directing the laser beam at the center of the internal surface.

4. A method according to claim 1, wherein the directing step includes the step of
    radially outwardly increasing the exposure of the laser beam on the internal surface.

5. A method according to claim 1, wherein the directing step comprises the step of
    directing the laser beam in an annular pattern onto the internal surface.

* * * * *